(12) United States Patent
Levine et al.

(10) Patent No.: US 8,587,439 B2
(45) Date of Patent: Nov. 19, 2013

(54) SYSTEMS, METHODS AND DEVICES FOR PROMOTING THERMOGENESIS

(75) Inventors: James A. Levine, Oronoco, MN (US); Paul H. Kane, Rochester, MN (US); Chinmay U. Manohar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1539 days.

(21) Appl. No.: 11/919,900

(22) PCT Filed: May 4, 2006

(86) PCT No.: PCT/US2006/017168
§ 371 (c)(1),
(2), (4) Date: Apr. 9, 2008

(87) PCT Pub. No.: WO2006/121758
PCT Pub. Date: Nov. 16, 2006

(65) Prior Publication Data
US 2009/0048538 A1  Feb. 19, 2009

Related U.S. Application Data

(60) Provisional application No. 60/678,018, filed on May 5, 2005.

(51) Int. Cl.
*G08B 23/00* (2006.01)

(52) U.S. Cl.
USPC ...................................................... 340/573.7

(58) Field of Classification Search
USPC .............. 600/513, 595, 523, 300; 33/512
See application file for complete search history.

(56) References Cited

U.S. PATENT DOCUMENTS

| | | | |
|---|---|---|---|
| 5,919,149 | A | 7/1999 | Allum |
| 6,095,985 | A | 8/2000 | Raymond et al. |
| 6,513,532 | B2 | 2/2003 | Mault et al. |
| 6,834,436 | B2 | 12/2004 | Townsend et al. |
| 2005/0240087 | A1 | 10/2005 | Keenan et al. |

FOREIGN PATENT DOCUMENTS

EP  1178597 A1 * 2/2002
WO  WO 2006/121758 A2  11/2006

OTHER PUBLICATIONS

Ainsworth et al., "Compendium of Physical Activities: classification of energy costs of human physical activities," *Med. Sci. Sports Exerc.*, 1993;25(1):71-80.
Ainsworth et al., "Compendium of Physical Activities: an update of activity codes and MET intensities," *Med. Sci. Sports Exerc.*, 2000;32(9 Suppl):S498-S516.

(Continued)

*Primary Examiner* — Brian Szmal
*Assistant Examiner* — Fangemonique Smith
(74) *Attorney, Agent, or Firm* — Mueting, Raasch & Gebhardt, P.A.

(57) ABSTRACT

Systems, methods and devices to measure and potentially promote thermogenesis, preferably non-exercise activity thermogenesis are disclosed. In the various embodiments, the present invention may rely on one or more sensors that detect a subject's body posture and/or activity. Feedback regarding the subject's posture and/or activity (relative to preferred postures and/or activity levels) may preferably be provided after the data is retrieved and analyzed. A power interlock may also be used to control delivery of electrical energy based on a subject's posture and/or activity level.

19 Claims, 3 Drawing Sheets

(56) References Cited

OTHER PUBLICATIONS

Bassett et al., "Validity of four motion sensors in measuring moderate intensity physical activity," *Med. Sci. Sports Exerc.*, 2000;32(9 Suppl):S471-S480.

Black et al., "Human energy expenditure in affluent societies: an analysis of 574 doubly-labelled water measurements," *Eur. J. Clin. Nutr.*, 1996;50(2):72-92.

Blundell et al., "Physical activity and regulation of food intake: current evidence," *Med. Sci. Sports Exerc.*, 1999;31(11 Suppl):S573-S583.

Bouten et al., "Assessment of energy expenditure for physical activity using a triaxial accelerometer," *Med. Sci. Sports Exerc.*, 1994;26(12):1516-1523.

Bouten et al., "Daily physical activity assessment: comparison between movement registration and doubly labeled water," *J. Appl. Physiol.*, 1996;81(2):1019-1026.

Consolazio, "Energy expenditure studies in military populations using Kofranyi-Michaelis respirometers," *Am. J. Clin. Nutr.*, 1971;24(12):1431-1437.

D'Alessio et al., "Thermic Effect of Food in Lean and Obese Men," *J. Clin. Invest.*, Jun. 1988;81(6):1781-1789.

Daniels, "Portable respiratory gas collection equipment," *J. Appl. Physiol.*, 1971;31(1):164-167.

Dauncey, "Activity and energy expenditure," *Can. J. Physiol. Pharmacol.*, 1990;68(1):17-27.

de Groot, et al., "A portable Lightweight Douglas Bag Instrument for Use During Various Types of Exercise," *Int. J. Sports. Med.*, 1983;4(2):132-134.

Dériaz et al., "Lean-body-mass composition and resting energy expenditure before and after long-term overfeeding," *Am. J. Clin. Nutr.*, 1992;56(5):840-847.

Donahoo et al., "Variability in energy expenditure and its components," *Curr. Opin. Clin. Nutr. Metab. Care*, 2004;7(6):599-605.

Douglas, "A method for determining the total respiratory exchange in man," *Prov. J. Physiol. Soc.*, Mar. 18, 1911;42:17-22.

Epstein, "Integrating Theoretical Approaches to Promote Physical Activity," *Am. J. Prev. Med.*, 1998;15(4):257-265.

Epstein et al., "Decreasing Sedentary Behaviors in Treating Pediatric Obesity," *Arch. Pediatr. Adolesc. Med.*, 2000;154(3):220-226.

Everhart et al., "Prevalence and Ethnic Differences in Gallbladder Disease in the United States," *Gastroenterology*, 1999;117(3):632-639.

Ford, "Some consequences of body size," *Am. J. Physiol.*, 1984;247(4 Pt 2):H495-H507.

Goran et al., "Effect of gender, body composition, and equilibration time on the $^2$H-to-$^{18}$O dilution space ratio," *Am J. Physiol.*, 1992;263(6 Pt 1):E1119-E1124.

Goran et al., "Deuterium exchange in humans: effect of gender, body composition and age," *Human Body Composition.*,1993;60(3):79-81.

Gretebeck et al., "Variability of some objective measures of physical activity," *Med. Sci. Sports Exerc.*, 1992;24(10):1167-1172.

Hill et al., "Thermic effect of food after ingested versus tube-delivered meals," *Am. J. Physiol.*, 1985;248(3 Pt 1):E370-E374.

Hill et al., "Environmental Contributions to the Obesity Epidemic," *Science*, May 29, 1998;280(5368):1371-1374.

Hubert et al., "Obesity as an Independent Risk Factor for Cardiovascular Disease: a 26-year Follow-up of Participants in the Framingham Heart Study," *Circulation*, 1983;67(5):968-977.

Jakicic et al., "Prescribing exercise in multiple short bouts versus one continuous bout: effects on adherence, cardiorespiratory fitness, and weight loss in overweight women," *Int. J. Obes. Relat. Metab. Disord.*, 1995;19(12):893-901.

Jéquier et al., "Indirect calorimetry," *Baillieres Clin. Endocrinol. Metab.*, 1987; 1(4):911-935.

Kinabo et al., "Thermic effect of food in man: effect of meal composition, and energy content," *Br. J. Nutr.*, 1990;64(1):37-44.

Kuczmarski et al., "Varying Body Mass Index Cutoff Points to Describe Overweight Prevalence Among U.S. adults: NHANES III (1988 to 1994)," *Obes. Res.*, Nov. 1997;5(6):542-548.

Levine et al., "Role of Nonexercise Activity Thermogenesis in Resistance to Fat Gain in Humans," *Science*, Jan. 8, 1999;283(5399):212-214.

Levine, et al., "Energy expenditure of nonexercise activity," *Am. J. Clin. Nutr.*, 2000; 72(6):1451-1454.

Levine et al., "Measurement of the components of nonexercise activity thermogenesis," *Am. J. Physiol Endocrinol Metab.*, 2001;281(4):E670-E675.

Levine et al., "Validation of the Tracmor triaxial accelerometer system for walking," *Med. Sci. Sports Exerc.*, 2001;33(9):1593-1597.

Levine et al., "Tracmor system for measuring walking energy expenditure," *Eur. J. Clin. Nutr.*, 2003;57(9):1176-1180.

Levine et al., "Interindividual Variation in Posture Allocation: Possible Role in Human Obesity," *Science*, Jan. 28, 2005;307(5709):584-586.

Lew et al., "Variations in mortality by weight among 750,000 men and women," *J. Chronic Dis.*, 1979;32(8):563-576.

Livingstone et al., "Potential contribution of leisure activity to the energy expenditure patterns of sedentary populations," *Br. J. Nutr.*, 1991;65(2):145-155.

Lum et al., "Accuracy of physiologic deadspace measurement in intubated pediatric patients using a metabolic monitor: Comparison with the Douglas bag method," *Crit. Care Med.*, 1998;26(4):760-764.

Mayer, "Physical activity and anthropometric measurements of obese adolescents," *Fed. Proc.*, Jan.-Feb. 1966;25(1):11-14.

McLaughlin et al., "Validation of the COSMED K4 b$^2$ Portable Metabolic System," *Int. J. Sports Med.*, 2001;22(4):280-284.

Melanson et al., "Validity of the Computer Science and Applications, Inc. (CSA) activity monitor," *Med. Sci. Sports Exerc.*, 1995;27(6):934-940.

Pambianco et al., "Accuracy and reliability of the Caltrac accelerometer for estimating energy expenditure," *Med. Sci. Sports Exerc.*, 1990;22(6):858-862.

Pelto et al., Eds. *Research Methods in Nutritional Anthropology*, Tokyo, Japan, 1989; cover page, title page and table of contents only, 3 pgs.

Ravussin et al., "Determinants of 24-hour Energy Expenditure in Man. Methods and Results Using a Respiratory Chamber," *J. Clin. Invest.*, Dec. 1986; 78(6):1568-1578.

Ravussin, "A NEAT Way to Control Weight?" *Science*, Jan. 28, 2005;307(5709): 530-531.

Reed et al., "Measuring the thermic effect of food," *Am. J. Clin. Nutr.*, 1996;63(2):164-169.

Rietjens et al., "Validation of a Computerized Metabolic Measurement System (Oxycon-Pro) During Low and High Intensity Exercise," *Int. J. Sports Med.*, 2001;22(4):291-294.

Schutz et al., "Spontaneous physical activity measured by radar in obese and control subject studied in a respiration chamber," *Int. J. Obes.*, 1982;6(1):23-28.

Shetty et al., "Energy requirements of adults: an update on basal metabolic rates (BMRs) and physical activity levels (PALs)," *Eur. J. Clin. Nutr.*, 1996;50 Suppl 1:S11-S23.

Sujatha et al., "Energy expenditure on household, childcare and occupational activities of women from urban poor households," *Br. J. Nutr.*, 2000;83(5):497-503.

Sun et al., "Modification of a whole room indirect calorimeter for measurement of rapid changes in energy expenditure," *J. App. Physiol.*, 1994;76(6):2686-2691.

Westerterp et al., "Physical activity assessment: Comparison between movement registration and doubly labeled water method," *Z. Ernährungswiss*, 1997;36(4):263-267.

Young et al., "The occurrence of sleep-disordered breathing among middle-aged adults," *N. Engl. J. Med.*, Apr. 29, 1993;328(17):1230-1235.

Zhang et al., "Measurement of Human Daily Physical Activity," *Obes. Res.*, 2003;11(1):33-40.

Ferro-Luzzi et al., "Seasonal Energy Deficiency in Ethiopian Rural Women," *European Journal of Clinical Nutrition*, 1990;44(Supp 1):7-18.

(56) References Cited

OTHER PUBLICATIONS

Marr et al., "Within- and Between-Person Variation in Dietary Surveys: Number of Days Needed to Classify Individuals," *Human Nutrition: Applied Nutrition*, 1986;40A:347-364.

Schoeller et al., "Precision of the Doubly Labelled Water method Using the Two-Point Calculation," *Human Nutrition: Clinical Nutrition*, 1987;41C:215-223.

Steele et al., "Bodies in motion: Monitoring daily activity and exercise with motion sensors in people with chronic pulmonary disease," *J. Rehab. Res. & Dev.*, Sep./Oct. 2003;40(5)Supp 2:45-58.

Strath et al., "Simultaneous heart rate-motion sensor technique to estimate energy expenditure," *Medicine & Science in Sports & Exercise*, Mar. 2001;2118-2123.

Zaki et al., "The Regulation of Food Intake and Correlated Energy Balance in Mice," *J. Vet Med. Sci.*, Feb. 1991;53(1):249-254.

\* cited by examiner

SYSTEMS, METHODS AND DEVICES FOR PROMOTING THERMOGENESIS

RELATED APPLICATION

The present application is a U.S. National Stage Application of International Application No. PCT/US2006/017168, filed May 4, 2006 and titled SYSTEMS, METHODS AND DEVICES FOR PROMOTING THERMOGENESIS, which claims the benefit under 35 U.S.C. §119(e) of U.S. Provisional Patent Application No. 60/678,018, filed May 5, 2005 and titled SYSTEMS, METHODS AND DEVICES FOR PROMOTING THERMOGENESIS, all of which are hereby incorporated by reference in their entirety.

The present invention relates to systems, methods and devices for promoting thermogenesis in a subject.

Non-exercise activity thermogenesis (NEAT), even in many exercisers, is the predominant constituent of activity thermogenesis and is the energy expenditure (or 'metabolism') associated with all the activities we undertake as vibrant, independent beings. NEAT includes the energy equivalent (EE) of occupation, leisure, sitting, standing, walking, talking, toe-tapping, playing guitar, dancing, and shopping. NEAT has an enormous variety of constituents and NEAT is likely to contribute substantially to the inter- and intra-personal variability in energy expenditure.

NEAT is highly variable, ranging from about 15% of total daily energy expenditure in very sedentary individuals to 50% or more of total daily energy expenditure in highly active (non-exercising) individuals. Even for similar sized people living in developed countries, NEAT can vary by >1500 kcal/day; about two-thirds of this variability occurs during work time (as so much of the day is spent at work) and a third occurs during leisure time.

The reason for this variability in NEAT is two-fold. First, there is marked variance in the energetic cost of sedentary versus active tasks. For an average overweight 40 year old person, an hour spent watching television (seated) will expend about 5-10 kcal/hour whereas that same person engaged in yard work would expend 100-200 kcal for the hour. Second, there is marked variability in the time allocated by different people to different tasks. For example, an individual might spent 10 hours or work time plus six hours of leisure time seated (160 kcal/day of NEAT) whereas, for example, a mail delivery person spends 10 hours per day ambulating and then gardens in the evening (1600 kcal/day of NEAT).

Examples of known physiological monitoring systems may be found in, e.g., U.S. Patent Application Publication No. US 2005/0240087 (Keenan et al.); U.S. Pat. No. 6,834,436 B2 (Townsend et al.); and in Levine et al., "Measurement of the Components of Nonexercise Activity Thermogenesis, Am. J. Physiol. Endocrinol Metab 2001, 218(4):E670-5.

SUMMARY OF THE INVENTION

The present invention provides systems, methods and devices to measure and potentially promote thermogenesis, preferably non-exercise activity thermogenesis. In the various embodiments, the present invention may rely on one or more sensors that detect a subject's body posture and/or activity. Feedback regarding the subject's posture and/or activity (relative to preferred postures and/or activity levels) may preferably be provided after the data is retrieved and analyzed.

Potential advantages of the present invention may include the ability to assist a subject with behavior modification that is consistent with increased Non-Exercise Activity Thermogenesis (NEAT). For example, through monitoring the subject's posture, it may be possible to provide feedback to the subject that promotes actions that increase the NEAT of the subject. For example, the system may monitor the subject's body position (e.g., sitting, lying down, standing, etc.) and record that data. At appropriate intervals, the collected data may be analyzed and used to provide motivation to the subject to engage in thermogenesis-producing postures (e.g., stand as opposed to remaining seated) or activity (e.g., walk, etc.). NEAT may be promoted by monitoring the subject's activities and body posture using a variety of sensors.

In some embodiments, the present invention provides a system and methods of use that include two (or more) posture sensing units and one (or more) activity sensing units. In use, each of the sensing units may be "independent" of the other sensing units, which means that data is not exchanged between the units or between a central controller. Rather, each sensing unit operates independently to monitor inclination or activity of a subject and store the data on-board the sensing unit. Methods of using such systems may include retrieving information from such sensing units for external processing using, e.g., a personal computer, dedicated data analysis device, etc.

Potential advantages of such systems and methods may include, e.g., the ability to monitor posture and activity in subjects without the need for more complicated, interconnected devices arrayed over the subject's body. Rather, the systems and methods of at least some embodiments of the present invention provide independent sensing units capable of collecting data that can be downloaded to an external processing device (e.g., personal computer, etc.). The data can then be analyzed to determine time spent in various postures and/or activity levels of the subject.

Other potential advantages of such distributed, independent systems may include, e.g., the ability to manufacture generic sensing units using the same components to achieve economies of scale in manufacturing, etc. The generic sensing units can preferably be configured (via, e.g., hardware, software, etc.) to function as posture sensors (by, e.g., sensing inclination of an accelerometer) or activity sensors (sensing, e.g., motion of the accelerometer relative to two or more axes).

In other embodiments, the present invention may provide power interlock systems and methods of controlling the flow of electricity to promote thermogenesis in a subject. Such systems may include an inclinometer and/or accelerometer adapted for attachment to a subject and an interlock switch that, when open, passes electric energy in response to output signals indicative of selected orientations of the inclinometer relative to gravitational force and/or output signals indicative of motion of the accelerometer. When closed, the interlock switch restricts the flow of electric energy.

Potential advantages of such power interlock systems and methods may include, e.g., promoting activity and/or selected postures by removing electrical power need to operate devices such as, e.g., televisions, computer monitors, lights, audio entertainment devices (e.g., stereos, personal music players, etc.), air conditioning, etc. unless the subject is in selected postures and/or exceeding selected activity levels. Restricting electrical power to such devices may provide subjects with additional motivation to engage in activities and/or postures considered to increase energy expenditure in the subject.

In one aspect, the present invention provides a method for monitoring body posture and activity. The method includes attaching two posture sensing units and one activity sensing unit to a subject. The posture sensing units and the activity sensing unit each include a housing having a power source located therein; an accelerometer located within the housing, the accelerometer operably connected to the power source; control electronics located within the housing operably connected to the accelerometer and the power source; resident memory located within the housing, the resident memory capable of receiving and storing data from the control electronics; optionally, a removable memory device operably connected to the control electronics and the resident memory; monitoring inclination of the accelerometers relative to gravity in each of the posture sensing units and storing inclination data related to the inclination in the resident memory; transferring the inclination data in the resident memory of each posture sensing unit to the removable memory device of the posture sensing unit; monitoring movement of the accelerometer in the activity sensing unit and storing activity data related to the movement in the resident memory of the activity sensing unit; optionally transferring the activity data in the resident memory of the activity sensing unit to the removable memory device of the activity sensing unit; and transferring the posture data and activity data to an external data processing device, which may optionally involve removing the optional removable memory device from each of the two posture sensing units and the activity sensing unit.

In another aspect, the present invention provides a system for monitoring non-exercise activity thermogenesis. The system includes three independent sensing units, wherein two of the three independent sensing units are configured to sense posture and one of the three independent sensing units is configured to sense movement. Each independent sensing unit includes a housing having a power source located therein; an accelerometer located within the housing, the accelerometer operably connected to the power source; control electronics located within the housing operably connected to the accelerometer and the power source, resident memory located within the housing, the resident memory capable of receiving and storing data from the control electronics; and an optional removable memory device operably connected to the control electronics and the resident memory such that data from the resident memory can be transferred to the removable memory device.

In another aspect, the present invention provides a power interlock system for promoting thermogenesis in a subject. The system includes an inclinometer adapted for attachment at a first body location, wherein the inclinometer provides output signals indicative of the orientation of the inclinometer relative to gravity; an accelerometer adapted to attachment at a body location, wherein the accelerometer provides output signals indicative of motion of the accelerometer; a connector adapted to connect to a source of electric energy; and an interlock switch that, when open, passes electric energy from the source to an outlet in response to output signals indicative of selected orientations of the inclinometer relative to gravitational force and/or output signals indicative of motion of the accelerometer and, when closed, restricts the flow of electric energy through the outlet.

In another aspect, the present invention provides a system for monitoring non-exercise activity thermogenesis. The system includes an inclinometer adapted for attachment at a first body location, wherein the inclinometer provides output signals indicative of the orientation of the inclinometer relative to gravitational force; an accelerometer adapted to attachment at a body location, wherein the accelerometer provides output signals indicative of motion of the accelerometer; a controller operably connected to the inclinometer and the accelerometer, wherein the controller receives the output signals from the inclinometer and the accelerometer. The controller further includes a memory unit operably connected to the controller, the memory unit capable of storing the amount of time the inclinometer is in one or more selected orientations and the amount of time the accelerometer is in motion. The system also includes a display unit operably connected to the controller, the display unit capable of displaying visual indicia indicative of the amount of time the inclinometer is in the one or more selected orientations; a self-contained power source operably connected to the controller; a transceiver operably connected to the controller, the transceiver capable of transmitting information from the controller to another device and receiving information from another device for delivery to the controller; and a compliance unit operably connected to the controller, the compliance unit capable of providing a compliance reminder based at least in part on the amount of time the inclinometer is in one or more selected orientations and/or the amount of time that motion is detected by the accelerometer.

In another aspect, the present invention provides a method for monitoring non-exercise activity thermogenesis. The method includes detecting the orientation of an inclinometer relative to gravitational force, wherein the inclinometer is attached at a body location; detecting motion using an accelerometer attached at a body location; storing collected data in a memory device on the subject, wherein the data includes the amount of time the inclinometer is in one or more selected orientations and/or the amount of time the accelerometer is in motion; displaying visual indicia on a display unit operably connected to the inclinometer and the accelerometer, wherein the visual indicia is indicative of the amount of time the inclinometer is in the one or more selected orientations; transmitting the data to a remote data collection location and optionally receiving information from a remote administrator; and providing reminders to the subject, the reminders based at least in part on the amount of time the inclinometer is in one or more selected orientations and/or the amount of time that motion is detected by the accelerometer.

These and other features and advantages of the present invention may be described in connection with a variety of exemplary embodiments of the invention described herein.

BRIEF DESCRIPTIONS OF THE FIGURES

DESCRIPTION OF EXEMPLARY EMBODIMENTS OF THE INVENTION

In the following description of exemplary embodiments of the invention, reference may be made to figures in which are shown specific embodiments in which the invention may be practiced. It is to be understood that other embodiments may be utilized and structural changes may be made without departing from the scope of the present invention.

Figure 1:
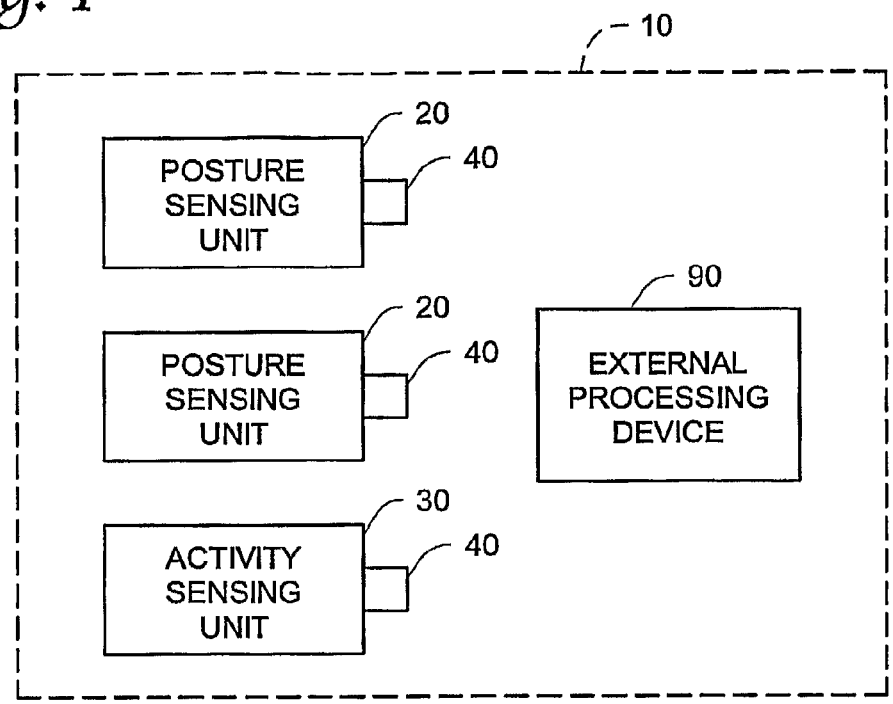
FIG. 1 is a block diagram of one exemplary posture and activity monitoring system according to the present invention.

At least some embodiments of the present invention may be in the form of a system, one exemplary embodiment of which is depicted in the block diagram of FIG. 1. Such systems according to the present invention may preferably include a set of independent sensing units that are used to collect data relating to posture and activity of a subject to which they are attached. As used in connection with the present invention, an "independent" sensing unit is a unit that is not in communication with the other sensing units in the system or with a central controller. In essence, each sensing unit operates independently to collect data relating to posture or activity. That data is then transferred out of the sensing unit at a selected time, preferably using, e.g., a removable memory device as described herein.

In the system 10 depicted in FIG. 1, two posture sensing units 20 are included along with an activity sensing unit 30. Although two posture sensing units 20 are included in the system 10, it should be understood that posture and activity sensing systems (and methods of using them) may employ more than two posture sensors 20 if desired. In general, though, two posture sensors, each of which preferably includes an inclinometer, should be sufficient to generally distinguish between the subject standing, sitting or lying down.

It may be preferred to attach one of the posture sensors 20 to the subject's torso or another part of the body that remains generally vertically oriented when the subject is standing or sitting upright (in, e.g., a desk chair) and that is generally horizontal when the subject is lying down. The other posture sensor 20 may then preferably be attached to one of the subject's thighs or another part of the body that is generally vertically oriented when the subject is standing and is generally horizontal when the subject is lying down or sitting upright (in, e.g., a desk chair).

Although only one activity sensing unit 30 is depicted in connection with the system 10, the systems of the present invention may use more than one activity sensing unit if so desired. In general, though, the systems may need only one activity sensing unit 30 to determine whether the subject is walking or otherwise ambulating.

The activity sensor 30 may be attached in a variety of locations on the subject's body, although it may be preferred to attach the activity sensing unit on the subject's torso or other location that does not typically move when the subject is standing still, seated or lying down, but that does move when the subject is ambulating. Locating the activity sensor on, e.g., a limb, may result in erroneous indications that the subject is walking if the limb is in motion while the subject is seated, standing, or lying down. An example of such a situation may be found if the activity sensor 30 were attached to a subject's leg and the subject were found to move the leg while seated or standing in one location.

Each of the posture sensing units 20 and the activity sensing unit 30 in the depicted system 10 may preferably include a removable memory device 40 on which data collected during operation of the sensing unit 30 can be stored.

The removable memory device 40 may also be used to configure a generic sensing unit to operate in a posture sensing mode or an activity sensing mode. As discussed herein, the removable memory device 40 may include hardware and/or software such that, when the removable memory device 40 is operably connected to the sensing unit, a configuration of the sensing unit into either a posture sensing unit 20 or an activity sensing unit 30 is accomplished.

The depicted system 10 also includes an optional external processing device 90 that may preferably be used to analyze the data collected by the posture sensing units 20 and the activity sensing unit 30. The external processing device 90 may take a variety of forms, although the external processing device may conveniently be in the form of, e.g., a personal computer or other digital data processor. The external processing device 90 may preferably includes data acquisition hardware and/or software capable of retrieving and analyzing the data stored on the removable memory devices 40 by the posture sensing units 20 and the activity sensing unit 30 in the system 10. The external processing device 90 may also preferably be capable of outputting the results of the data analyses to the subject or a third party (e.g., care provider, etc.). In other instances, the external processing device 90 may be in a form other than a personal computer, e.g., a personal data assistant (PDA), cellular telephone, digital music player, etc. with sufficient data processing capabilities.

Figure 2:
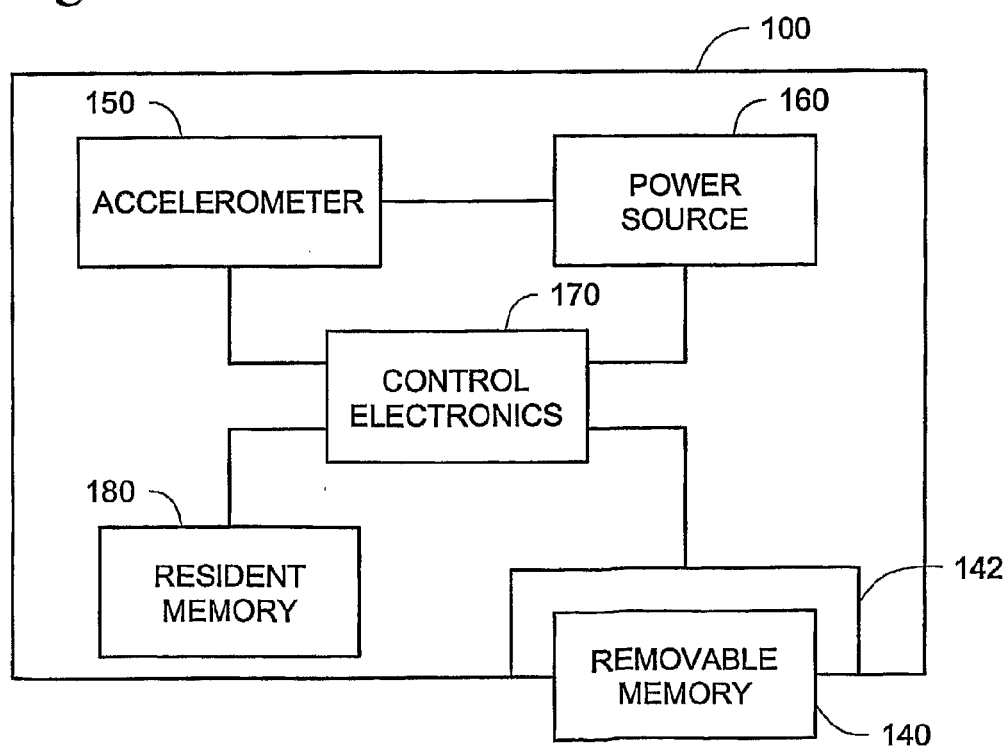
FIG. 2 is a block diagram of components in one exemplary sensing unit for use in a posture and activity monitoring system according to the present invention.

The components of one exemplary sensing unit 100 that can be configured for use as a posture sensing unit or an activity sensing unit is depicted in FIG. 2. The sensing unit 100 includes, in addition to the removable memory device 140, an accelerometer 150, a power source 160, control electronics 170 and resident memory 180. These components may preferably be contained within a single housing that can be conveniently attached to a subject using, e.g., straps, adhesives, specialized garments, etc.

The power source 160 preferably provides power to operate the control electronics 170 and the accelerometer 150. The power source 160 may be in the form of, e.g., a battery, capacitor, etc. The control electronics 170 may be provided in the form of a microprocessor, an Application Specific Integrated Circuit (ASIC) state machine, a gate array, custom circuitry, etc. Regardless of its exact form, the control electronics 170 may preferably provide timing functions, convert analog data received from the accelerometer to digital form (if the accelerometer output is analog), and be capable of managing data transfer to the resident memory 180 and the removable memory device 140. The control electronics 170 may also potentially perform any other selected functions, e.g., providing alerts to the subject, operating a display, managing communication with external devices, etc.

The resident memory 180 may preferably be in the form of flash memory operably connected to receive and provide data to the control electronics 170. The removable memory device 140 may also preferably be in the form of a portable flash memory device that can interface through, e.g., a connector 142, with the control electronics 170. Although flash memory may be currently preferred for the removable memory device 140 and the resident memory 180 because of its relatively low power consumption, other forms of memory storage may alternatively be used, e.g., magnetic tapes or disks, optical data storage, etc.

The removable memory device 140, which is preferably a portable flash memory device, may take any form. Examples of potentially suitable forms may include, e.g., Secure Digital (SD) cards, Compact Flash (CF) cards, etc. The connector 142 used to interface the removable memory device 140 with the control electronics 170 is preferably compatible with the type or types of portable flash memory devices to be used with the sensing unit 100.

In systems in which the sensing unit 100 is to be capable of operating either as a posture sensing device or an activity sensing device, the accelerometer 150 may preferably be a 3-axis accelerometer. One example of suitable accelerometer is, e.g., a 3-axis MEMS KXM52-1010 accelerometer chip available from Kionix, Inc., Ithaca, N.Y.

To be used in a posture sensing unit, the accelerometer 150 preferably has the ability to operate as an angle detector (inclinometer) that can be used in the posture sensing units of the present invention. This may be achieved, e.g., by measuring the acceleration of earth's gravitational field. When the selected axis of the accelerometer is oriented parallel to (the force vector of) gravity, the accelerometer senses maximum acceleration (1 g). When the accelerometer 150 is rotated such that the axis is no longer parallel to gravity (i.e. the accelerometer axis is inclined relative to gravity), the earth's gravitation field exerts its force at an angle other than zero degrees to the selected axis and, thus, the acceleration measured along that inclined axis decreases.

To be used in an activity sensing unit, the accelerometer 150 is preferably operated as a triaxial accelerometer to detect body movement of the subject to which the sensing unit 100 is attached. When used to detect movement, displacements of the accelerometer along all of the x, y and z axes may preferably be monitored, although movement in two axes may, in some instances be sufficient to detect movement of the subject.

It may be preferred that the removable memory device 140 used in the sensing unit 100 be capable of providing the instructions (e.g., software) required to configure the sensing unit 100 to operate as either a posture sensing device or an activity sensing device. Potential benefits of such an approach include, e.g., simplification of manufacturing of the sensing units—all of which may be constructed with the same components.

Alternatively, it should be understood that the instructions (e.g., software) used to operate the sensing unit may be contained in the resident memory 180, with the selection between a posture sensing unit or an activity sensing unit being made by an alternate technique, e.g., in the control electronics itself, using DIP switches, etc.

Figure 3:
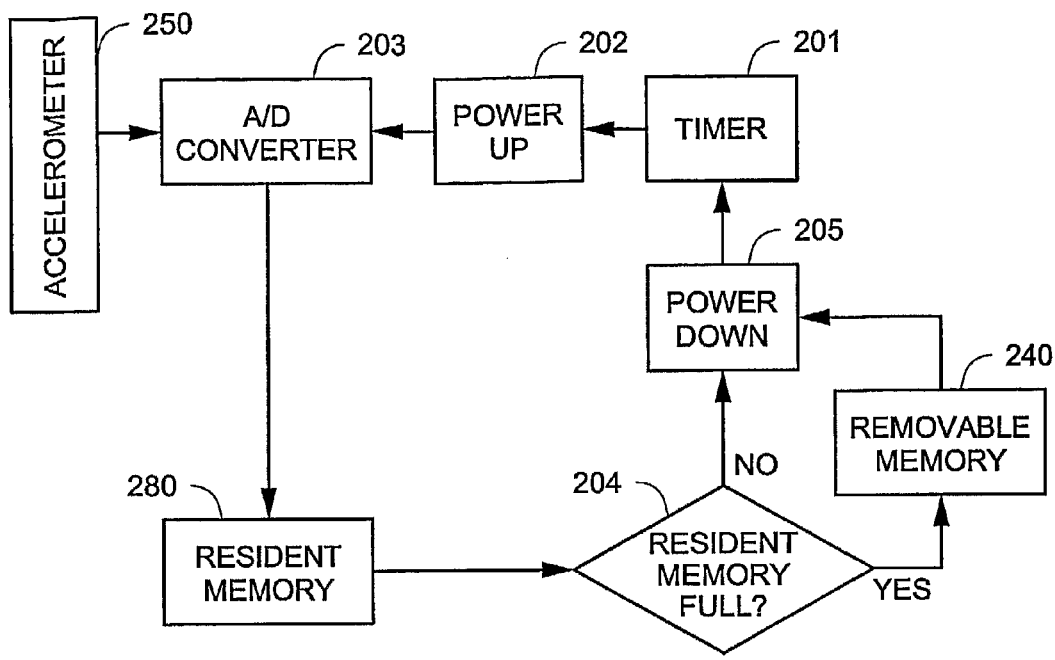
FIG. 3 is a flow chart/component diagram illustrating operation of an exemplary sensing unit used in a posture and activity monitoring system according to the present invention.

FIG. 3 depicts an exemplary data acquisition event loop for a sensing unit employing, e.g., a microprocessor that includes a CPU, timer, and analog-to-digital (A/D) converter. The sensing unit may preferably be controlled using a timer 201 to trigger data acquisition events. To conserve power, it may be preferred that the CPU and other components in the sensing unit power down between data acquisition events. As a result, when the timer 201 indicates that a data acquisition event is needed, the system powers up 202 such that analog data received from the accelerometer 250 can be converted into digital form using the A/D converter 203. The digitized data from the A/D converter 203 is then stored in the resident memory 280.

In systems that include a removable memory device 240 (as discussed herein), it may be helpful to determine whether the resident memory 280 provided in the sensing unit is reaching a selected level as indicated in decision block 204. If the resident memory 280 is at a selected capacity, the accumulated data may be transferred from the resident memory 280 to the removable storage device 240. If the resident memory 280 has not yet reached the selected level, then the system may move towards a power down state 205 until the timer 201 signals the start of the next data acquisition event.

Figure 4:
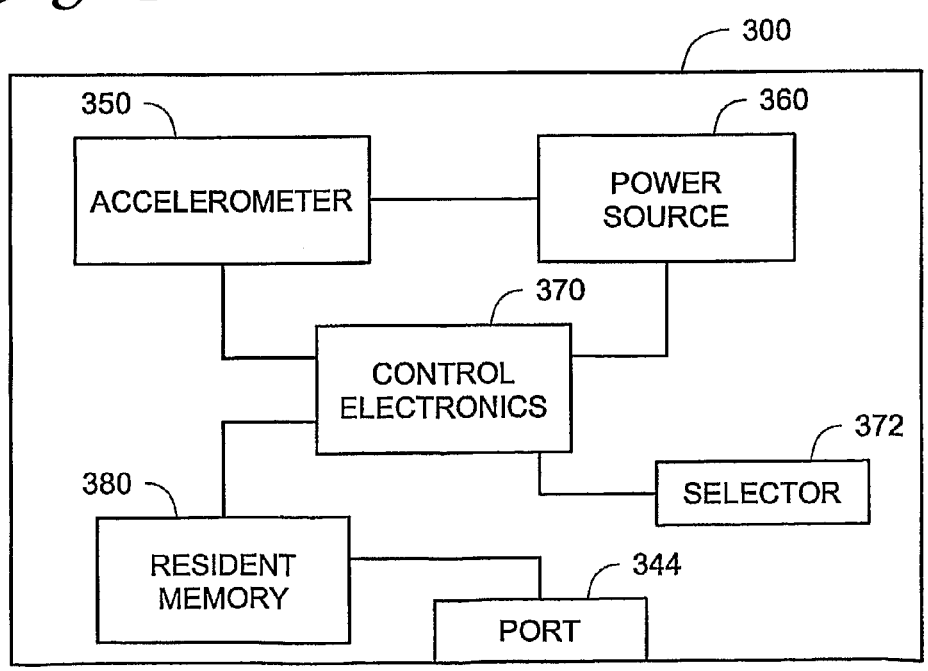
FIG. 4 is a block diagram of components in an alternative sensing unit.

An alternative sensing unit 300 is depicted in the block diagram of FIG. 4. Many of the components are similar to those included in the sensing unit 100 depicted in FIG. 2 and described herein. For example, the discussions regarding the accelerometer 350, power source 360 and control electronics 370 generally apply to those components in the sensing unit 300 as well.

One difference in the system 300 (from system 100) is the absence of a removable memory device. In system 300, the resident memory 380 is preferably used for data storage. Stored data can be removed from the system 300 using, e.g., data port 344. In some instances, data port may be a physical structure, e.g., a USB connector, IEEE 1394 connector, serial port, parallel port, etc. In other instances, the data port could be replaced by, e.g. a wireless data port (using, e.g., BLUETOOTH technology, infrared, radio frequency, etc.).

Because the system 300 no longer includes the additional data storage capacity provided by the removable memory device of the system 100 depicted in FIG. 2, the capacity of the on-board resident memory 380 may preferably be increased.

Another optional component depicted in the system of FIG. 3 is a selector 372 that may be used to configure the system 300 for use as a posture sensing unit or an activity sensing unit. The selector 372 may take a physical form such as, e.g., DIP switches, etc. Alternatively, the selector may be embodied in software provided to the control electronics, contained within the resident memory 380, in the control electronics, etc.

Figure 5:
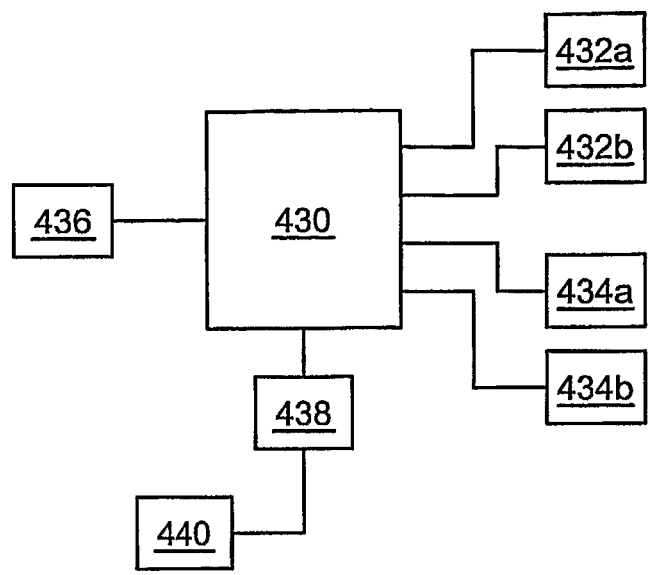
FIG. 5 is a block diagram of a power interlock system that may be used in connection with posture and/or activity sensing in connection with the present invention.

FIG. 5 is a block diagram of another exemplary system according to the present invention in the form of a power interlock. The system of FIG. 5 preferably includes an interlock switch 430 that is connected to a power source using connector 436. The connector 436 may preferably take the form of, e.g., a cord and plug adapted for use with conventional outlets such as those found in homes, offices, etc. (which provide 120V alternating current at 50/60 hz) or any other suitable power source (e.g., 220V power sources, etc.).

The interlock switch 438 controls the flow of electric energy to an outlet 438 to which an external device 440 such as a television, computer monitor, lights, etc. are connected. In use, it may be preferred that the interlock switch 430 provide electric energy to the outlet 438 when selected signals are received from posture sensors 432a & 432b and/or activity sensors 434a & 434b. As such, the flow of electric energy to the external device 440 may be interrupted if the selected signals are not received. The interlock system may preferably include a buffer or delay device to prevent excessive cycling of the interlock switch 430 between the open and closed states.

Although accelerometers (operated as either motion sensors or inclinometers) are described in connection with the systems of the present invention, it will be understood that other sensors capable of detecting body position and/or movement may be used in place of accelerometers.

Although the memory devices described herein may preferably be in the form of flash memory, the memory used in connection with the present invention may be of any suitable type, although it may be preferred that the data be stored in a digital format using, e.g., magnetic drives, tape drives, optical storage, etc.

The sensing units of the present invention may also include a display capable of displaying visual indicia. The display may be used to display, e.g., data indicative of the amount of time an inclinometer is in the one or more selected orientations, amount of time that movement is detected, or other information.

Some systems of the present invention may preferably include one or more self-contained power sources operably connected to the various components. The power sources may be in the form of batteries, capacitive storage units, etc. In some instances, the power sources may be self-regenerating using movement (e.g., as in self-winding watches). Other power sources may be recharged using, e.g., photovoltaic cells, RF energy, microwave energy, etc.).

Some systems of the present invention may also include a transceiver that may be used to transmit information from the system to another device and/or receive information from another device. The transceiver may be used to deliver data to a remote location (e.g., physician, researcher, etc.). Information received by the transceiver from a remote location may be used to, e.g., program one or more components in the system, reset goal times for certain body postures and/or movement, etc.

A compliance unit may also be included in systems of the present invention. A compliance unit capable of providing a compliance reminder to the subject using the system based at least in part on the amount of time the sensors indicate that the subject's body is in one or more selected postures and/or the amount of time that motion is detected. The compliance unit may take a variety of forms, e.g., an audible indicator, a vibrating component, a light, etc. that can be used to signal the subject to, e.g., consult the display unit to view information displayed there.

The systems of the present invention may conveniently be integrated into one or more garments worn by the subject. Alternatively, the components of the system may be attached to the patient by any suitable technique or techniques, e.g., using adhesives, straps, etc.

Still other systems of the present invention may include a power interlock, wherein the power interlock passes electric energy in response to output signals indicative of selected orientations of the subject's body and/or output signals indicative of motion by the subject. The power interlock may be used to control power delivery to, e.g., a television, computer monitor, etc. Use of a power interlock may be used to promote selected body positions (e.g., standing as opposed to sitting) or to promote movement of the subject (e.g., walking on a treadmill). The power interlock may include a buffer or delay device that allows electric energy to pass for a selected period of time in the absence of output signals indicative of selected orientations of the subject's body and/or output signals indicative of motion by the subject.

Many of the functions of the systems as described herein may potentially be integrated into an existing device that includes a microprocessor. Examples of such devices may include, e.g., a cellular telephone, pager, digital music player (e.g., an MP3 player), a watch, a PDA (e.g., a PALM PILOT, etc.) Many of these devices include microprocessors, displays, etc. Alternatively, such devices could potentially be used as the external processing device described in connection with the system of FIG. 1.

The methods may also involve storing collected data in a memory device on the subject, wherein the data comprises the amount of time the subject's body is in one or more selected orientations and/or the amount of time the subject is in motion. The data may be periodically delivered directly to a storage device located locally (i.e., in the vicinity of the subject but not directly attached to the subject) or remotely (i.e., in a different building, city, state, etc.).

The methods may further involve displaying visual indicia on a display unit, wherein the visual indicia is indicative of the amount of time the subject's body is in the one or more selected orientations and/or in motion This information may be delivered to the subject to improve compliance with recommended body positions and/or motion.

Figure 6:
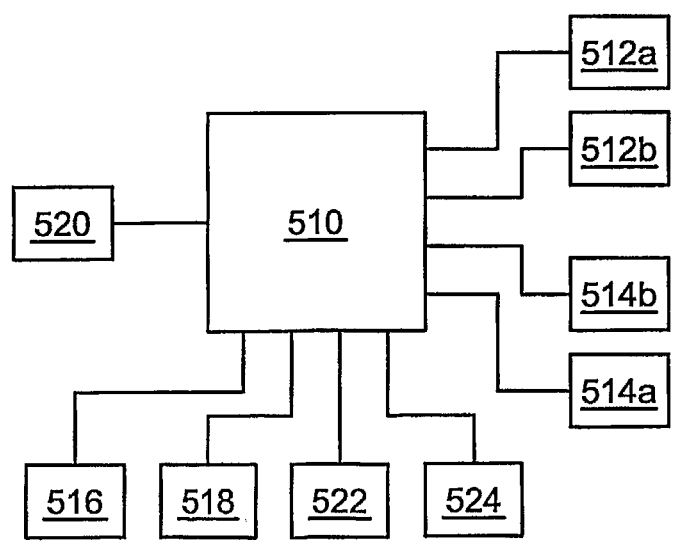
FIG. 6 is a block diagram of another exemplary posture and activity monitoring system.

FIG. 6 is a schematic diagram of another exemplary system that includes a controller 510 that may be, e.g., implemented using a microprocessor, software, hard-wired circuitry, combinations thereof, etc. The controller 510 is operably connected to one or more body position sensors 512a & 512b (e.g., inclinometers) that can be attached to a subject's body to detect body position/posture. The controller 510 is also operably connected to one or more motions sensors (e.g., accelerometers) that can be attached to a subject's body or otherwise positioned to detect motion by the subject.

Also depicted in the exemplary system of FIG. 6 is an optional memory unit 516 adapted to store information such as the subject's body position, time spent in selected body positions, etc. The memory unit 516 may take any suitable form, although it may be preferred that the memory be digital in nature, e.g., flash memory, magnetic or optical drives, magnetic disks/tapes, etc.

A display unit 518 is also depicted in connection with the exemplary system. The display unit 518 may also take any suitable form, although it may be preferred that the display unit be capable of displaying alphanumeric characters (e.g., an LCD panel, etc.).

The system of FIG. 6 also preferably includes a self-contained power source 520 that supplies power to the various components of the system. It may be preferred that a single power source 520 be used, although a distributed power supply approach may be used where, e.g., one or more individual components are provided with their own power sources. The power source 520 may preferably be in the form of a battery, although other power sources may also be used.

An optional transceiver 522 may also be operably connected to the controller 510 to transmit and/or receive data to a remote administrator. The transceiver 522 may be used to reprogram the controller 510, monitor power levels in power source 520, etc. The transceiver 522 may operate using any suitable technique or techniques. It may be operated using, e.g., telephony, radio frequencies, microwaves, etc. Transceiver 522 may in some instances require connection to an existing communication network, e.g., telephone lines, the Internet or other computer networks, etc.

The system of FIG. 6 may also include a compliance unit 524 operably connected to the controller 510. The compliance unit 524 is preferably capable of providing a compliance reminder to a subject based at least in part on data obtained from the sensors. The compliance reminder may be provided visually (using, e.g., a light, display unit 516, etc.), audibly (e.g., using beeps, alarms, tones, etc.), or through tactile sensations (e.g., vibration, thermally, etc.), at least in part on the amount of time the inclinometer is in one or more selected orientations and/or the amount of time that motion is detected by the accelerometer.

The methods of the present invention may also involve transmitting the data to a remote data collection location and, optionally, receiving information from a remote administrator. The remote administrator may, for example, adjust activity goals for the subject based on recent performance, etc.

The methods may also involve providing reminders to the subject, the reminders based at least in part on the amount of time the subject is in one or more selected orientations and/or the amount of time that the subject is in motion.

As used herein and in the appended claims, the singular forms "a," "and," and "the" include plural referents unless the context clearly dictates otherwise. Thus, for example, reference to "a" or "the" component or feature may include one or more of the components or features and equivalents thereof known to those skilled in the art.

All references and publications identified herein are expressly incorporated herein by reference in their entirety into this disclosure. Exemplary embodiments of this invention are discussed and reference has been made to possible variations within the scope of this invention. It should be understood that the various components identified within each exemplary system may be introduced in an any selected combination into another system of the present invention. For example, the sensing units described in connection with the system 10 of FIG. 1 may incorporate functions such as, e.g., displays and compliance components described in connection with the system of FIG. 6. Many other variations are also possible within the scope of the present invention.

These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A system for monitoring non-exercise activity thermogenesis, the system comprising:
    an inclinometer adapted for attachment at a first body location, wherein the inclinometer provides output signals indicative of the orientation of the inclinometer relative to gravitational force;
    an accelerometer adapted to attachment at a body location, wherein the accelerometer provides output signals indicative of motion of the accelerometer;
    a power interlock, wherein the power interlock passes electric energy in response to output signals indicative of selected orientations of the inclinometer relative to gravitational force and/or output signals indicative of motion of the accelerometer;
    a controller operably connected to the inclinometer and the accelerometer, wherein the controller receives the output signals from the inclinometer and the accelerometer, the controller further comprising:
    a memory unit operably connected to the controller, the memory unit capable of storing the amount of time the inclinometer is in one or more selected orientations and the amount of time the accelerometer is in motion;
    a display unit operably connected to the controller, the display unit capable of displaying visual indicia indicative of the amount of time the inclinometer is in the one or more selected orientations;
    a self-contained power source operably connected to the controller;
    a transceiver operably connected to the controller, the transceiver capable of transmitting information from the controller to another device and receiving information from another device for delivery to the controller; and
    a compliance unit operably connected to the controller, the compliance unit capable of providing a compliance reminder based at least in part on the amount of time the inclinometer is in one or more selected orientations and/or the amount of time that motion is detected by the accelerometer.

2. A system according to claim 1, further comprising a second inclinometer adapted for attachment at a second body location, wherein the second inclinometer provides output signals indicative of the orientation of the second inclinometer relative to gravitational force, wherein the controller is operably connected to the second inclinometer, wherein the memory unit is capable of storing the amount of time the second inclinometer is in one or more selected orientations, and wherein the compliance reminder is based at least in part on the amount of time the second inclinometer is in one or more selected orientations.

3. A system according to claim 2, further comprising a plurality of accelerometers adapted for attachment at a plurality of body locations, wherein each accelerometer is operably attached to the controller.

4. A system according to claim 1, further comprising a plurality of inclinometers adapted for attachment at a plurality of body locations, wherein each inclinometer is operably attached to the controller.

5. A system according to claim 1, wherein the inclinometer and/or accelerometer are integrated into a garment adapted to be worn by a subject.

6. A system according to claim 1, wherein the inclinometer is operably connected to the controller through a wireless connection.

7. A system according to claim 1, wherein the accelerometer is operably connected to the controller through a wireless connection.

8. A system according to claim 1, wherein the power interlock comprises a buffer that allows electric energy to pass for a selected period of time in the absence of output signals indicative of selected orientations of the inclinometer relative to gravitational force and/or output signals indicative of motion of the accelerometer.

9. A system according to claim 1, wherein the controller is integrated into a device selected from the group consisting of cellular telephone, pager, digital music player; watch, and PDA.

10. A method for monitoring non-exercise activity thermogenesis, the method comprising:
    detecting the orientation of an inclinometer relative to gravitational force, wherein the inclinometer is attached at a body location;
    detecting motion using an accelerometer attached at a body location;
    storing collected data in a memory device on the subject, wherein the data comprises the amount of time the inclinometer is in one or more selected orientations and/or the amount of time the accelerometer is in motion;
    displaying visual indicia on a display unit operably connected to the inclinometer and the accelerometer, wherein the visual indicia is indicative of the amount of time the inclinometer is in the one or more selected orientations;
    transmitting the data to a remote data collection location and optionally receiving information from a remote administrator;
    providing reminders to the subject, the reminders based at least in part on the amount of time the inclinometer is in one or more selected orientations and/or the amount of time that motion is detected by the accelerometer;
    permitting the flow of electric energy through a power interlock in response to output signals indicative of selected orientations of the inclinometer relative to gravitational force and/or output signals indicative of motion of the accelerometer and restricting the flow of electric energy in the absence of the output signals.

11. A power interlock system for promoting thermogenesis in a subject, wherein the system comprises:
    an inclinometer adapted for attachment at a first body location, wherein the inclinometer provides output signals indicative of the orientation of the inclinometer relative to gravity;
    an accelerometer adapted to attachment at a body location, wherein the accelerometer provides output signals indicative of motion of the accelerometer; and
    a connector adapted to connect to a source of electric energy;
    an interlock switch that, when open, passes electric energy from the source to an outlet in response to output signals indicative of selected orientations of the inclinometer relative to gravitational force and/or output signals indicative of motion of the accelerometer and, when closed, restricts the flow of electric energy through the outlet; and optionally comprising a buffer that retains the interlock switch open for a selected period of time in the absence of output signals indicative of selected orientations of the inclinometer relative to gravitational force and/or output signals indicative of motion of the accelerometer.

12. A method according to claim 10, wherein the inclinometer and/or accelerometer are integrated into a garment worn by a subject.

13. A method according to claim 10, wherein the method comprises passing electric energy through the power interlock for a selected period of time in the absence of the output signals.

14. A method according to claim 10, wherein the electric energy permitted to flow is delivered at 120V or 220V.

15. A method according to claim 10, wherein the electric energy is delivered through an outlet to an external device.

16. A method according to claim 10, wherein the electric energy permitted to flow is delivered to an external device through an outlet at 120V or 220V.

17. A system according to claim 1, wherein the power interlock comprises an interlock switch configured to control electric energy at 120V or 220V.

18. A system according to claim 1, wherein the power interlock comprises an outlet configured to deliver electric energy at 120V or 220V.

19. A system according to claim 1, wherein the power interlock comprises an interlock switch configured to control electric energy at 120V or 220V and an outlet configured to deliver electric energy at 120V or 220V.

* * * * *